(12) United States Patent
Chen et al.

(10) Patent No.: US 11,793,149 B2
(45) Date of Patent: Oct. 24, 2023

(54) SOYBEAN CULTIVAR 'UA54I19GT'

(71) Applicant: THE BOARD OF TRUSTEES OF THE UNIVERSITY OF ARKANSAS, Little Rock, AR (US)

(72) Inventors: Pengyin Chen, Fayetteville, AR (US); Leandro Mozzoni, Fayetteville, AR (US); Sandra L. Florez-Palacios, Springdale, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 44 days.

(21) Appl. No.: 17/164,038

(22) Filed: Feb. 1, 2021

(65) Prior Publication Data
US 2022/0240473 A1    Aug. 4, 2022

(51) Int. Cl.
*A01H 5/10* (2018.01)
*A01H 6/54* (2018.01)

(52) U.S. Cl.
CPC ............... *A01H 6/542* (2018.05); *A01H 5/10* (2013.01)

(58) Field of Classification Search
None
See application file for complete search history.

(56) References Cited

U.S. PATENT DOCUMENTS 9,107,374 B2 *  8/2015  Hancock ................ A01H 6/542
9,907,261 B2 *  3/2018  Wooten, Jr. ............... A01H 5/10
9,907,283 B1 *  3/2018  Eby ....................... A01H 6/542

OTHER PUBLICATIONS

Carlin, J.F. et al. 2019. Arkansas soybean performance tests. Arkansas soybean performance tests 2019. Research Series 664. Fayetteville: Arkansas Agricultural Experiment Station, University of Arkansas System. (Year: 2019).*
Burgess, B., et al. 2021. Mississippi soybean variety trials, 2020. Information bulletin 556. Mississippi State University. MS Agricultural and Forestry Experiment Station. Retrieved from https://www.mafes.msstate.edu/publications/information-bulletins/ib0556.pdf.
Carlin, J.F., et al. 2019. Arkansas soybean performance tests. Arkansas soybean performance tests 2019. Research Series 664. Fayetteville: Arkansas Agricultural Experiment Station, University of Arkansas System.
Carlin, J.F., et al. 2021. Arkansas soybean performance tests. Arkansas soybean performance tests 2020. Research Series 673. Fayetteville: Arkansas Agricultural Experiment Station, University of Arkansas System.

* cited by examiner

*Primary Examiner* — Cynthia E Collins
(74) *Attorney, Agent, or Firm* — Quarles & Brady LLP

(57) ABSTRACT

A soybean cultivar designated UA54i19GT is disclosed herein. The present invention provides seeds, plants, and plant parts derived from soybean cultivar UA54i19GT. Further, it provides methods for producing a soybean plant by crossing UA54i19GT with itself or another soybean variety. The invention also encompasses any soybean seeds, plants, and plant parts produced by the methods disclosed herein, including those in which additional traits have been transferred into UA54i19GT through the introduction of a transgene, through mutagenesis, or by breeding UA54i19GT with another soybean cultivar.

19 Claims, 2 Drawing Sheets

SOYBEAN CULTIVAR 'UA54I19GT'

BACKGROUND OF THE INVENTION

The present invention relates to a new and distinctive soybean cultivar, designated UA54i19GT.

The soybean (*Glycine max*) is the world's leading source of vegetable oil and protein meal. The oil extracted from soybeans is used for cooking oil, margarine, and salad dressings. Soybean oil is also processed for many industrial uses, including as an ingredient for paints, plastics, fibers, detergents, cosmetics, lubricants, and biodiesel fuel. Designing and producing soybean oil derivatives with improved functionality and oliochemistry is a rapidly growing field.

Soybeans are used as a food source for both humans and animals. For example, soybeans are widely used as a source of protein in poultry, swine, and cattle feed. During processing of whole soybeans, the fibrous hull is removed and the oil is extracted. The remaining soybean meal comprises carbohydrates and approximately 50% protein. For human consumption, soybean meal is made into soybean flour, which is processed into protein concentrates. These soybean proteins offer a healthy, less expensive replacement for animal protein in meats and dairy products.

Soybean is an important and valuable field crop. A continuing goal of soybean plant breeding is to develop stable, high yielding soybean cultivars that are agronomically sound. To accomplish this goal, soybean plants with traits that result in superior cultivars must be developed.

SUMMARY OF THE INVENTION

The present invention provides a novel soybean cultivar designated UA54i19GT. The invention encompasses the seeds, plants, and plant parts of soybean cultivar UA54i19GT, as well as plants with essentially all of the physiological and morphological characteristics of UA54i19GT.

This invention also provides methods for producing a soybean plant by planting a plurality of seeds or by crossing soybean UA54i19GT with itself or another soybean line. Any plant breeding methods using soybean cultivar UA54i19GT are part of this invention, including selfing, backcrosses, hybrid production, and crosses to populations. All plants and seeds produced using soybean cultivar UA54i19GT as a parent are within the scope of this invention, including gene-converted plants of UA54i19GT. Methods for introducing a gene into UA54i19GT (i.e., either through traditional breeding or transformation) and methods for mutagenizing UA54i19GT are also provided herein.

In still another aspect, the present invention provides regenerable cells for use in tissue culture of soybean plant UA54i19GT, as well as soybean plants regenerated from these tissue cultures.

DEFINITIONS

Figure 1:
FIG. 1 is a photograph showing the pre-foundation increase (approximately 0.1 acre) of R13-14635RR (UA54i19GT) in Stuttgart, Ark.

To provide a clear and consistent understanding of the specification and claims, the following definitions are provided:

Backcrossing. A process in which a breeder repeatedly crosses hybrid progeny back to a parental line. For example, a first generation ($F_1$) hybrid may be crossed with one of the parental lines used to produce the $F_1$ hybrids.

Breeding. The genetic manipulation of living organisms.

BU/A. Bushels per Acre. The seed yield in bushels/acre is the actual yield of the grain at harvest.

Cell. As used herein, this term includes isolated cells, cells grown in tissue culture, and cells that comprise a plant or plant part.

Cotyledon. A cotyledon is a type of seed leaf. The cotyledon contains the food storage tissues of the seed.

Cultivar. Used interchangeably with "variety". Refers to plants that are defined by the expression of the characteristics resulting from a given genotype or combination of genotypes, distinguished from any other plant grouping by the expression of at least one characteristic.

Cross-pollination. Fertilization by the union of two gametes from different plants.

Diploid. A cell or organism having two sets of chromosomes.

Embryo. The plant embryo is the part of a seed or bud that contains the earliest forms of the new plant's roots, stem and leaves.

Essentially all of the physiological and morphological characteristics. A plant having "essentially all the physiological and morphological characteristics" of the cultivar exhibits the characteristics of the cultivar with the exception of any characteristics derived from a converted gene.

F#. Denotes a filial generation, wherein the # is the generation number. For example, F1 is the first filial generation.

Gene. Refers to a unit of inheritance corresponding to a distinct sequence of DNA or RNA nucleotides that form part of a chromosome. A gene may encode a polypeptide or a nucleic acid molecule that has a function in the cell or organism.

Gene-converted. Describes a plant wherein essentially all of the desired morphological and physiological characteristics of a parental variety are maintained with the exception of a single trait that was transferred into the variety via backcrossing or genetic engineering.

Genotype. Refers to the genetic constitution of a cell or organism.

Haploid. A cell or organism having a single set of unpaired chromosomes.

Herbicide-tolerant. Used interchangeably with the term "herbicide-resistant" to indicate that a plant or part thereof is capable of growing in the presence of an amount of herbicide that normally causes growth inhibition or phytotoxicity in a non-herbicide-tolerant (e.g., a wild-type) plant or part thereof. Levels of herbicide that normally inhibit growth of a non-tolerant plant are known and readily determined by those skilled in the art. Examples include the quantity of herbicide or rate of application recommended by herbicide manufacturers. The maximum level or rate of herbicide application is the amount of herbicide that would normally inhibit the growth or cause phytotoxicity of a non-herbicide tolerant plant.

Hilum. This refers to the scar left on the seed that marks the place where the seed was attached to the pod prior to the seed being harvested.

Hybrid. Refers to the offspring or progeny of genetically dissimilar plant parents or stock produced as the result of controlled cross-pollination as opposed to a non-hybrid seed produced as the result of natural pollination.

Hypocotyl. A hypocotyl is the portion of an embryo or seedling between the cotyledons and the root. Therefore, it can be considered a transition zone between shoot and root.

Lodging. The percentage of plant stems that are leaning or have fallen to the ground before harvest. Lodging is determined by visual scoring, in which crops are rated from 0% (all plants standing) to 100% (all plant in plot lying flat on the soil surface). Lodged plants are difficult to harvest and reduce yield and grain quality. Lodging resistance is also referred to "standability".

Maturity Date. Plants are considered mature when 95% of the pods have reached their mature color. The number of days are calculated either from August 31 or from the planting date.

Maturity Group. This refers to an agreed upon industry division of groups of soybean varieties based on zones in which they are adapted, primarily according to day length or latitude. They consist of very long day length varieties (Groups 000, 00, 0), and extend to very short day length varieties (Groups VII, VIII, IX, X).

Oil or Oil Percent. Soybean seeds contain a considerable amount of oil. Oil is measured by NIR spectrophotometry and is reported as a percentage basis.

Pedigree. Refers to the lineage or genealogical descent of a plant.

Plant. As used herein, the term "plant" includes plant cells, plant protoplasts, and plant cell tissue cultures from which soybean plants can be regenerated; plant calli, plant clumps and plant cells that are intact in plants; and parts of plants, such as embryos, pollen, ovules, flowers, glumes, panicles, leaves, stems, roots, root tips, anthers, and pistils.

Plant height. Measured in centimeters from the soil surface to the tip of the extended panicle at harvest.

Plant parts. Includes, without limitation, protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

Pod. This refers to the fruit of a soybean plant. It consists of the hull or shell (pericarp) and the soybean seeds.

Progeny. Includes an $F_1$ soybean plant produced from the cross of two soybean plants, as well as plants produced from subsequent generational crosses (e.g., $F_2$, $F_3$, $F_4$, $F_5$, $F_6$, $F_7$, $F_8$, $F_9$, and $F_{10}$) with the recurrent parental line.

Protein Percent. Soybean seeds contain a considerable amount of protein. Protein is generally measured by NIR spectrophotometry and is reported on an as is percentage basis.

Pubescence. This refers to a covering of very fine hairs closely arranged on the leaves, stems, and pods of the soybean plant.

Regeneration. Refers to the development of a plant from tissue culture.

Relative Maturity (RM). A numerical value that is assigned to a soybean cultivar based on comparisons with the maturity values of other varieties. The number preceding the decimal point in the RM refers to the maturity group. The number following the decimal point refers to the relative earliness or lateness within each maturity group. For example, a 3.0 is an early group III cultivar, while a 3.9 is a late group III cultivar.

Seeds. Includes seeds and plant propagules of all kinds including, but not limited to, true seeds, seed pieces, suckers, corms, bulbs, fruit, tubers, grains, cuttings, cut shoots and the like. However, in preferred embodiments, it refers to true seeds.

Trait. Refers to an observable and/or measurable characteristic of an organism. For example, the present invention describes plants that have a trait that make them resistant to fluazifop herbicides.

Transgenic. Describes an organism or cell that contains genetic material that has been artificially introduced.

Wild-type. When made in reference to a gene, "wild-type" refers to a functional gene common throughout a plant population and, thus, arbitrarily designated the "normal" or "wild-type" form of the gene.

Yield (Bushels/Acre). The yield in bushels/acre is the actual yield of the grain at harvest.

Check mean: is defined as the average performance for the entries flagged as checks in the trial. Checks are commercial products, developed by the Arkansas Agricultural Experiment Station or by other private or public breeding companies and institutions. Checks could be conventional non-GMO materials, or could have one of different herbicide-tolerant transgenic trait packages.

Grand mean: is defined as the average performance for all entries and checks planted in a given trial.

Traited competitor: is defined as the average performance for entries flagged as checks that also carry a herbicide-tolerance transgenic trait package.

Canopy is measured when plants are at the R6 stage, prior to dropping leaves, and is measured using a categorical scale of "narrow", "intermediate", and "wide".

Flood severity score is measured by subjecting the plots to flood for 1 week, and then rating for chlorosis and necrosis using a 0 to 9 scale, where 0 are no symptoms of necrosis and necrosis, and 9 indicates plant death.

DETAILED DESCRIPTION OF THE INVENTION

The present invention provides a novel soybean cultivar designated UA54i19GT. The invention encompasses both the seeds of this cultivar and plants grown from these seeds. The invention further encompasses any soybean plant having essentially all of the physiological and morphological characteristics soybean cultivar UA54i19GT.

As used herein, the term plant includes plant cells, plant protoplasts, plant cell tissue cultures from which soybean plants can be regenerated, plant calli, plant clumps, and parts of plants, such as leaves, stems, roots, root tips, anthers, pistils, seed, grain, embryo, pollen, ovules, cotyledon, hypocotyl, pod, flower, shoot, tissue, petiole, cells, meristematic cells, and the like.

Development and Characterization of Soybean Cultivar UA54i19GT

R13-14635RR (which is to be released as 'UA54i19GT') is a glyphosate-tolerant MG5.4 indeterminate early-maturity group V (relative maturity 5.4) soybean cultivar that is broadly adapted and moves south very well. UA54i19GT has medium-tall height, great standability, good phenotypic looks, and a good disease package, including stem canker tolerance and moderate resistance to peanut root knot nematode. In addition, UA54i19GT has better than average response to flooding at vegetative stages. UA54i19GT is a 4.7 bushels per acre (bu/ac) upgrade compared to UA5414RR of similar maturity.

Table 1 describes the parentage and breeding history for R13-14635RR (UA54i19GT), while Table 2 lists phenotypic, disease, and stress traits. FIG. 1 shows the pre-foundation increase (approximately 0.1 acre) of UA54i19GT in Stuttgart, Ark.

Figure 2:
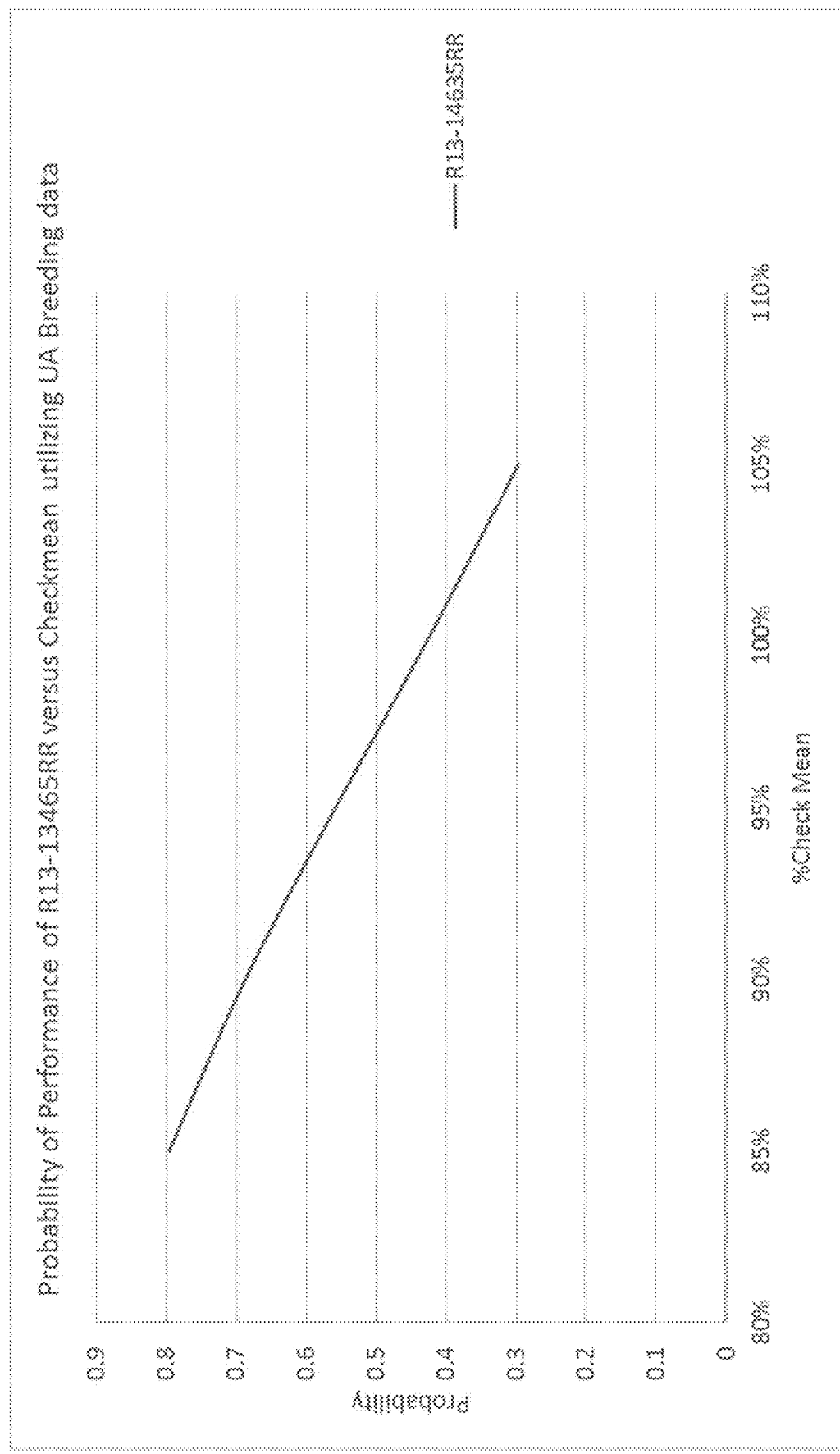
FIG. 2 is a graph showing the probability of performance as a percent of the check mean for R13-14635RR (UA54i19GT) based on breeding datasets. The probability of yield levels were calculated utilizing the 2015 to 2019 breeding dataset. Checks used in this analysis are listed in Table 3.

In over five years of testing, UA54i19GT yielded 64.4 bu/ac compared to a check mean of 66.3 bu/ac (difference: −1.9 bu/ac; p=0.001), which is 97% of check mean. In those trials, UA54i19GT matured three days later than the mean of the test (32.4 vs 29.4 days; p=0.140). Yield, plant height and lodging averages of UA54i19GT are presented in Table 3. Performance data for UA54i19GT in Official Variety Testing (VT) and United States Department of Agriculture (USDA) Uniform trials are presented in Table 4. On average, in VT and USDA trials, UA54i19GT performed better on silt loam soils (98% of grand mean in 14 experiments), as compared to clay soils (86% of grand mean in 4 environments). In addition, UA54i19GT seems to prefer southern environments, for it averaged 99% of grand mean in VT and USDA trial locations south of Interstate 40 (n=12 experiments). UA54i19GT significantly outperformed previous glyphosate-tolerant releases in breeding trials; see Table 5a and Table 5b for head-to-head comparisons of UA54i19GT with UA5414RR and with UA5715GT. FIG. 2 presents the probability of performance as a percent of the check mean for UA54i19GT based on breeding datasets. FIG. 3 presents the probabilities of revenue per acre for R13-14635RR and for the average traited competitor, as calculated from the 2017 and 2019 Variety Testing (VT) dataset.

TABLE 1

Breeding history of variety R13-14635RR (UA54i19GT).

| Generation | Year | Description |
|---|---|---|
| Cross | 2010 | The cross LEO 2939-04S809 × R04-572 was made in Fayetteville, AR |
| $F_1$ | 2011 | Plants were grown in Fayetteville, AR and advanced using bulk |
| $F_2$ | 2012 | Plants were grown in Kibler, AR and advanced using bulk |
| $F_3$ | 2012/13 | Plants were grown in a winter nursery in Costa Rica and advanced using single plant selection |
| $F_{3:4}$ | 2013 | Plants were grown in progeny rows in Stuttgart, AR. The line number 14635 was selected based on agronomic characteristics including, plant height, lodging, plot uniformity, and general disease resistance |

TABLE 2

Phenotypic description of variety R13-14635RR (UA54i19GT).

Morphology

| | |
|---|---|
| Relative Maturity | 5.4 |
| Flower Color | White |
| Pubescence Color | Gray |
| Hilum Color | Buff |
| Pod Color | Tan |
| Hypocotyl Color | Green |
| Seed Coat Color | Yellow |
| Seed Coat Luster | Dull |
| Seed Shape | Spherical flattened |
| Seed Size (g/100 seed) | 14.4 |
| Leaf Color | Green |
| Canopy | Intermediate |
| Growth Habit | Indeterminate |

Disease and Stress

Resistant to stem canker
Moderately resistant to peanut root-knot nematode
Moderately susceptible to Soybean Cyst Nematode (SCN) race 3
Susceptible to SCN race 5
Susceptible to southern root-knot nematode
(source: 2017 USDA Soybean Uniform Southern States Tests)
Better than average tolerance to flooding at vegetative stages
(flood severity score 5.9 vs. 6.4 test mean, p = 0.08)

TABLE 3

Agronomic traits of variety R13-14635RR and selected checks in 2014-19.

| | Yield (bu/ac) | | | | | | | Height (in) | | | | | Lodging (1 = erect to 5 = prostrate) | | | | |
|---|---|---|---|---|---|---|---|---|---|---|---|---|---|---|---|---|---|
| Entry | 2019 | 2018 | 2017 | 2016 | 2015 | 2014 | Mean | 2017 | 2016 | 2015 | 2014 | Mean | 2017 | 2016 | 2015 | 2014 | Mean |
| R13-14635RR (UA54i19GT) | 68.0 | 61.7 | 69.3 | 59.9 | 60.3 | 76.4 | 65.9 | 42 | 42 | 43 | 34 | 40 | 1.5 | 1.0 | 1.3 | 1.0 | 1.2 |
| AG4632 | . | . | . | 64.4 | . | . | 64.4 | . | 43 | . | . | 43 | . | 2.5 | . | . | 2.5 |
| P48A60X | 79.2 | . | . | . | . | . | 79.2 | . | . | . | . | . | . | . | . | . | . |
| AG4934/ AG49X6* | . | 66.4 | 77.6 | 62.5 | 56.3 | . | 65.7 | 38 | 45 | 43 | . | 42 | 1.5 | 1.5 | 1.3 | . | 1.4 |
| AG51X8/ CZ5147LL* | 66.7 | 72.6 | . | . | . | . | 69.7 | . | . | . | . | . | . | . | . | . | . |
| P52A05X | 79.1 | . | . | . | . | . | 79.1 | . | . | . | . | . | . | . | . | . | . |
| AG5335/ AG53X6/ P53A67X* | 73.4 | 62.4 | . | 61.9 | 63.2 | 67.6 | 65.7 | . | 38 | 41 | 31 | 37 | . | 1.0 | 1.1 | 1.5 | 1.2 |
| AG5535/P5555/ AG55X7* | . | 66.8 | 72.2 | 67.1 | . | . | 68.7 | 34 | 31 | . | 33 | 3.0 | 1.0 | . | . | 2.0 |
| AG56X8 | 75.9 | 67.4 | . | . | . | . | 71.7 | . | . | . | . | . | . | . | . | . | . |
| 95Y70 | . | . | . | . | 60.2 | . | 60.2 | . | . | 40 | . | 40 | . | . | 3 | . | 2.7 |
| AG5831 | . | . | . | . | . | 65.3 | 65.3 | . | . | . | 26 | 26 | . | . | . | 1.0 | 1.0 |
| AG59X7 | . | 54.8 | . | . | . | . | 54.8 | . | . | . | . | . | . | . | . | . | . |
| CHECK MEAN | 74.8 | 65.1 | 74.8 | 62.3 | 59.9 | 66.5 | | | | | | | | | | | |
| CV | 6.6 | 5.0 | 7.7 | 8.3 | 7.7 | 7.0 | | | | | | | | | | | |
| LSD | 6.7 | 3.1 | 5.7 | 3.4 | 3.1 | 6.4 | | | | | | | | | | | |
| GRAND MEAN | 70.3 | 61.7 | 63.8 | 57.6 | 56.1 | 63.8 | | | | | | | | | | | |
| No. Environments | 2 | 4 | 6 | 5 | 4 | 2 | | | | | | | | | | | |

*AG49X6 in 2018; CZ 5147LL in 2019; AG5335 in 2015; P53A67X in 2019; AG53X6 in 2018; AG5335 in 2015 and 2016; AG55X7 in 2018; P5555 in 2017

TABLE 4

Yield (bu/ac) of the variety R13-14635RR in USDA Southern Uniform Soybean MG V (UT5) Test in 2017 and Arkansas and Texas Soybean Performance Tests in 2017 and 2019.

| Test | Location | Soil Type | # Entries | R13-14635RR Rank | R13-14635RR Yield | Grand mean Yield | % Grand mean | LSD |
|---|---|---|---|---|---|---|---|---|
| 17UT5 | Belle Mina | Silt loam | 29 | 18 | 62.0 | 63.3 | 98 | 5.5 |
|  | Bossier City | Very fine sandy loam | 29 | 9 | 66.8 | 62.6 | 107 | 10.5 |
|  | Jackson | Fine sandy loam | 29 | 19 | 73.6 | 75.2 | 98 | 8.8 |
|  | Kesier | Clay | 29 | 18 | 67.2 | 67.6 | 99 | 7.9 |
|  | Knoxville | Silt loam | 29 | 14 | 62.9 | 62.8 | 100 | 9.0 |
|  | Pittsburg | Silt loam | 29 | 17 | 50.5 | 53.4 | 95 | 5.4 |
|  | Plymouth | Silt loam | 29 | 22 | 53.6 | 55.1 | 97 | 8.9 |
|  | Portageville | Silt loam | 29 | 17 | 72.0 | 72.2 | 100 | 6.7 |
|  | Portageville | Clay | 29 | 24 | 39.7 | 42.5 | 93 | 8.1 |
|  | Springfield | Silt loam | 29 | 5 | 65.1 | 61.2 | 106 | 7.6 |
|  | Stoneville | Clay | 29 | 29 | 37.0 | 53.8 | 69 | 10.9 |
|  | Stuttgart | Silt loam | 29 | 12 | 70.8 | 69.8 | 101 | 4.7 |
|  | Suffolk | Sandy loam | 29 | 9 | 61.3 | 57.6 | 106 | 13.2 |
|  | Tallassee | Fine sandy loam | 29 | 9 | 42.7 | 39.6 | 108 | 11.4 |
|  | Warsaw | Loam | 29 | 16 | 60.8 | 61.6 | 99 | 13.4 |
| 17ARVT | Stuttgart | Silt loam | 28 | 25 | 69.2 | 72.8 | 95 | 3.3 |
|  | Rohwer | Silt loam | 28 | 24 | 49.8 | 54.8 | 91 | 6.4 |
|  | Kibler | Silt loam | 28 | 25 | 70.9 | 73.7 | 96 | 6.0 |
| 19TXVT | College Station | Silty clay loam | 48 | 22 | 41.0 | 39.0 | 105 | 9.9 |
|  | Wharton | Loam | 48 | 11 | 31.0 | 27.0 | 115 | 5.7 |
| 19ARVT | Keiser | Clay | 19 | 14 | 74.7 | 77.4 | 97 | 20.9 |
|  | Marianna | Silt loam | 19 | 14 | 65.0 | 68.4 | 95 | 11.7 |
|  | Pine Tree | Silt loam | 19 | 10 | 64.4 | 63.7 | 101 | 12.7 |
|  | Rohwer | Silt loam | 22 | 10 | 64.8 | 64.2 | 101 | 17.6 |
|  | Stuttgart DRY | Silt loam dryland | 19 | 7 | 42.2 | 40.6 | 104 | 6.2 |
|  | Stuttgart | Silt loam | 19 | 16 | 62.0 | 64.1 | 97 | 12.0 |

TABLE 5a

Head-to-head comparison of yield (bu/ac) between R13-14635RR and UA5414RR in Arkansas breeding trials.

| R13-14635RR (UA54i19GT) Yield (bu/ac) | UA 5414RR Yield (bu/ac) | Difference (bu/ac) | # Comparisons | Total years | p-value |
|---|---|---|---|---|---|
| 67.8 | 63.2 | 4.7 | 27 | 2 | 0.0372 |

TABLE 5b

Head-to-head comparison of yield (bu/ac) between R13-14635RR and UA5715GT in Arkansas breeding trials.

| R13-14635RR (UA54i19GT) Yield (bu/ac) | UA5715GT Yield (bu/ac) | Difference (bu/ac) | # Comparisons | Total years | p-value |
|---|---|---|---|---|---|
| 63.8 | 61.0 | 2.8 | 57 | 3 | 0.0123 |

Methods

This present invention provides methods for producing soybean plants. In some embodiments, these methods involve crossing a first parent soybean plant with a second parent soybean plant wherein either the first or second parent soybean plant is a soybean plant of the line UA54i19GT. Further, both first and second parent soybean plants can come from the soybean cultivar UA54i19GT. Still further, this invention also is directed to methods for producing a soybean cultivar UA54i19GT-derived soybean plant by crossing soybean cultivar UA54i19GT with a second soybean plant and growing the progeny seed, and repeating the crossing and growing steps with the soybean cultivar UA54i19GT-derived plant from 0 to 7 times. Thus, any such methods using the soybean cultivar UA54i19GT are part of this invention: selfing, backcrosses, hybrid production, crosses to populations, and the like. All plants produced using soybean cultivar UA54i19GT as a parent are within the scope of this invention, including plants derived from soybean cultivar UA54i19GT. Advantageously, the soybean cultivar is used in crosses with other, different, soybean cultivars to produce first generation ($F_1$) soybean seeds and plants with superior characteristics.

In some embodiments, a UA54i19GT progeny plant is selected that has molecular markers, morphological characteristics, and/or physiological characteristics in common with UA54i19GT (e.g., those listed in Table 2). Techniques such as RFLP-enhanced selection, genetic marker enhanced selection (e.g., SSR markers), and the making of double haploids may be utilized to identify progeny that share particular traits with UA54i19GT.

Further, this invention provides methods for introducing a desired trait into soybean cultivar UA54i19GT. This may be accomplished using traditional breeding methods, such as backcrossing (see Breeding Methods section below). Alternatively, the desired trait may be introduced by transforming the soybean cultivar with a transgene (see Transformation Methods section below), or by mutagenizing a gene within the soybean's genome (see Mutagenesis Methods section below). The transgenic or mutant cultivar produced by these methods may be crossed with another cultivar to produce a new transgenic or mutant cultivar. Alternatively, the transgene or mutant gene could be moved into another cultivar using traditional backcrossing techniques.

Optionally, any of the disclosed methods may further comprise additional steps involving producing soybean seed from the resulting soybean plants and/or planting the soybean seed.

The present invention encompasses all plants, or parts thereof, produced by the methods described herein, as well as the seeds produced by these plants. Further, any plants derived from soybean cultivar UA54i19GT or produced from a cross using cultivar UA54i19GT are provided. This includes genetic variants, created either through traditional breeding methods or through transformation, as well as plants produced in a male-sterile form. Notably, this includes gene-converted plants developed by backcrossing.

The present invention also encompasses progeny of soybean cultivar UA54i19GT comprising a combination of at least two UA54i19GT traits selected from those listed in the Tables and Detailed Description of the Invention, wherein the progeny soybean plant is not significantly different from UA54i19GT for said traits, as determined at the 5% significance level when grown in the same environment. One of skill in the art knows how to compare a trait between two plant varieties to determine if there is a significant difference between them (Fehr and Walt, Principles of Cultivar Development, pp. 261-286 (1987)). Molecular markers or mean trait values may be used to identify a plant as progeny of UA54i19GT. Alternatively, progeny may be identified through their filial relationship with soybean cultivar UA54i19GT (e.g., as being within a certain number of breeding crosses of soybean cultivar UA54i19GT). For example, progeny produced by the methods described herein may be within 1, 2, 3, 4, or 5 breeding crosses of soybean cultivar UA54i19GT.

Any of the seeds, plants, or plant parts provided may be utilized for human food, livestock feed, and as a raw material in industry (see Industrial Uses section below). The present invention also encompasses methods of producing a commodity plant product. Exemplary commodity plant products that can be produced from soybean cultivar UA54i19GT include, but are not limited to, protein concentrate, protein isolate, soybean hulls, meal, flour or oil.

Tissue Culture

The present invention provides tissue cultures of regenerable cells or protoplasts produced from soybean cultivar UA54i19GT. As is well known in the art, tissue culture of soybean can be used for the in vitro regeneration of a soybean plant. Thus, such cells and protoplasts may be used to produce plants having the physiological and morphological characteristics of soybean variety UA54i19GT. The soybean plants regenerated by these methods are also encompassed by the present invention.

As used herein, the term "tissue culture" describes a composition comprising isolated cells or a collection of such cells organized into parts of a plant. Exemplary tissues for culture include protoplasts, calli, plant clumps, and plant cells. Culture of various soybean tissues and regeneration of plants therefrom is well known in the art.

Methods for culturing plant tissues are known in the art. General descriptions of such methods are provided, for example, by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement*, 3rd Edition; Sprague, et al., (Eds. pp. 345-387 American Society of Agronomy Inc., 1988).

Breeding Methods

The goal of soybean breeding is to develop new, superior soybean cultivars and hybrids. A superior cultivar is produced when a new combination of desirable traits is formed within a single plant variety. Desirable traits may include higher seed yield, resistance to diseases and insects, better stems and roots, tolerance to low or high temperatures, herbicide resistance, and better agronomic characteristics or grain quality.

The breeding methods used with the present invention may involve a single-seed descent procedure, in which one seed per plant is harvested and used to plant the next generation. Alternatively, the methods may utilize a multiple-seed procedure, in which one or more seeds harvested from each plant in a population is threshed together to form a bulk which is used to plant the next generation.

Use of soybean cultivar UA54i19GT in any plant breeding method is encompassed by the present invention. The choice of a breeding or selection method will depend on several factors, including the mode of plant reproduction, the heritability of the trait(s) being improved, and the type of cultivar used commercially (e.g., $F_1$ hybrid cultivar, pureline cultivar). Popular selection methods include pedigree selection, modified pedigree selection, mass selection, recurrent selection, backcrossing, or a combination thereof.

Pedigree selection is commonly used for the improvement of self-pollinating crops. Two parents are crossed to produce an $F_1$ population. An $F_2$ population is produced by selfing one or several $F_1$'s. Selection of the best individuals may begin in the $F_2$ population; then, beginning in the $F_3$ generation, the best individuals in the best families are selected. Replicative testing of families can begin in the $F_4$ generation to make selection of traits with low heritability more effective. At an advanced stage of inbreeding (e.g., $F_6$ or $F_7$), the best lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population, which is often subjected to additional cycles of selection.

Backcrossing is commonly used to transfer genes for highly heritable traits into a desirable homozygous cultivar or inbred line. The term "backcrossing" refers to the repeated crossing of hybrid progeny back to one of the parental plants, referred to as the recurrent parent. The plant that serves as the source of the transferred trait is called the donor parent. After the initial cross, individuals possessing the transferred trait are selected and repeatedly crossed to the recurrent parent. The resulting plant is expected to have the attributes of the recurrent parent along with the trait transferred from the donor parent.

Transformation Methods

As is noted above, the present invention provides plants and seeds of soybean cultivar UA54i19GT in which additional traits have been transferred. While such traits may be selected for using traditional breeding methods, they may also be introduced as transgenes. "Transgenes" include both foreign genes and additional or modified versions of native genes. Plants can be genetically engineered to have a wide variety of traits of agronomic interest including, without limitation, herbicide resistance; insect resistance; resistance to bacterial, fungal, or viral disease; modified fatty acid metabolism; modified carbohydrate metabolism; male sterility or male fertility; waxy starch; enhanced nutritional quality (e.g., altered fatty acid profile or antioxidant content); industrial usage; yield stability; yield enhancement; and stress resistance. Many examples of genes that confer such traits have been described in the literature and are well known in the art. Exemplary transgenes include, without limitation, a gene conferring resistance to imidazolinone, dicamba, sulfonylurea, glyphosate, glufosinate, triazine, benzonitrile, cyclohexanedione, phenoxy propionic acid, or L-phosphinothricin; a gene encoding a *Bacillus thuringiensis* polypeptide; a gene encoding phytase, FAD-2, FAD-3, galactinol synthase, or a raffinose synthetic enzyme; and a gene conferring resistance to soybean cyst nematode, brown stem rot, *Phytophthora* root rot, soybean mosaic virus, or sudden death syndrome. Alternatively, transgenic soybean plants in which a gene is silenced (e.g., via knockout or antisense technology) or transgenic soybean plants that express a foreign protein for commercial production may be generated using soybean cultivar UA54i19GT.

Transgenes are typically introduced in the form of an expression vector. As used herein, an "expression vector" is DNA comprising a gene operatively linked to a regulatory element (e.g., a promoter). The expression vector may contain one or more such gene/regulatory element combinations. The expression vector may also include additional sequences, such as a signal sequence or a tag, that modify the protein produced by the transgene. The vector may be a plasmid, and can be used alone or in combination with other plasmids.

Expression vectors include at least one genetic marker operably linked to a regulatory element (e.g., a promoter) that allows transformed cells containing the vector to be recovered by selection. In some embodiments, negative selection, i.e., inhibiting growth of cells that do not contain the selectable marker gene, is utilized. Negative selection markers include, for example, genes that result in detoxification of a chemical agent (e.g., an antibiotic or an herbicide) and genes that result in insensitivity to an inhibitor. Exemplary negative selection genes include neomycin phosphotransferase II (nptII), hygromycin phosphotransferase, gentamycin acetyl transferase, streptomycin phosphotransferase, and aminoglycoside-3'-adenyl transferase. In other embodiments, positive selection, i.e., screening for the product encoded by a reporter gene, is utilized. Exemplary reporter genes include β-glucuronidase, β-galactosidase, luciferase, chloramphenicol acetyltransferase, and Green Fluorescent Protein (GFP).

Transgene expression is typically driven by operably linking the transgene to a promoter within the expression vector. However, other regulatory elements may also be used to drive expression, either alone or in combination with a promoter. As used herein, a "promoter" is a region of DNA upstream of a transcription start site that is involved in recognition and binding of RNA polymerase for transcription initiation. Any class of promoter may be selected to drive the expression of a transgene. For example, the promoter may be "tissue-specific", "cell type-specific", "inducible", or "constitutive". Those of skill in the art know how to select a suitable promoter based the particular circumstances and genetic engineering goals.

Methods for producing transgenic plants are well known in the art. General descriptions of plant expression vectors, reporter genes, and transformation protocols can be found in Gruber, et al., "Vectors for Plant Transformation", in *Methods in Plant Molecular Biology & Biotechnology* in Glich, et al., (Eds. pp. 89-119, CRC Press, 1993). Methods of introducing expression vectors into plant tissue include direct gene transfer methods, such as microprojectile-mediated delivery, DNA injection, and electroporation, as well as the direct infection, or co-cultivation of plant cells with *Agrobacterium tumefaciens*, described for example by Horsch et al., *Science*, 227:1229 (1985). Descriptions of *Agrobacterium* vector systems and methods for *Agrobacterium*-mediated gene transfer are provided by Gruber, et al., supra.

Mutagenesis Methods

Mutagenesis is another method of introducing new traits into soybean cultivar UA54i19GT. The goal of artificial mutagenesis is to increase the rate of mutation for a desired characteristic. Mutation rates can be increased by many different means including temperature, long-term seed storage, tissue culture conditions, radiation (e.g., X-rays, Gamma rays, neutrons, Beta radiation, or ultraviolet radiation), or chemical mutagens (e.g., base analogues such as 5-bromo-uracil, related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, and acridines. Once a desired trait is generated through mutagenesis, the trait may then be incorporated into existing germplasm by traditional breeding techniques. Details of mutation breeding can be found in Fehr, "Principles of Cultivar Development," Macmillan Publishing Company (1993). In addition, mutations created in other soybean plants may be transferred to soybean cultivar UA54i19GT using backcrossing.

Industrial Uses

The seed of soybean cultivar UA54i19GT, the plant produced from the seed, the hybrid soybean plant produced from the crossing of the cultivar with any other soybean plant, hybrid seed, and various parts of the hybrid soybean plant can be utilized for human food, livestock feed, and as a raw material in industry. The soybean seeds produced by soybean cultivar UA54i19GT can be crushed, or a component of the soybean seeds can be extracted for use in a commodity plant product, such as protein concentrate, protein isolate, soybean hulls, meal, flour, or oil.

Soybean cultivar UA54i19GT can be used to produce soybean oil. To produce soybean oil, the soybeans are harvested and cracked, adjusted for moisture content, rolled into flakes, and the oil is solvent-extracted from the flakes with commercial hexane. The oil is then refined, blended for specific applications, and sometimes hydrogenated. Soybean oils are used domestically and exported, sold as "vegetable oil," and used in a wide variety of processed foods.

Soybean cultivar UA54i19GT can be used to produce soybean meal. After oil is extracted from whole soybeans, the remaining material (referred to as "meal") is "toasted" and ground in a hammer mill. Soybean meal is essential in American production methods of growing farm animals (e.g., poultry, swine, and catfish) on an industrial scale. Ninety-eight percent of the U.S. soybean crop is used for livestock feed. Soybean meal is also used in lower-end dog foods. Soybean meal produced from soybean cultivar UA54i19GT can also be used to produce soybean protein concentrate and soybean protein isolate.

In addition, soybean cultivar UA54i19GT can be used to produce soy flour. Defatted soy flour is obtained from solvent extracted flakes, and contains less than 1% oil. Full-fat soy flour is made from unextracted, dehulled beans, and contains about 18% to 20% oil. Low-fat soy flour is made by adding back some oil to defatted soy flour. The lipid content varies according to specifications, usually between 4.5% and 9%. High-fat soy flour can also be produced by adding back soybean oil to defatted flour at the level of 15%. Lecithinated soy flour is made by adding soybean lecithin to defatted, low-fat or high-fat soy flours to increase their dispersibility and impart emulsifying properties. Soy flour is the starting material for production of soy concentrate and soy protein isolate.

Soybean cultivar UA54i19GT can be used to produce edible protein products for human consumption. These products offer a healthier, less expensive replacement for animal protein in meats, as well as in dairy-type products. The soybeans produced by soybean cultivar UA54i19GT can be processed to produce a texture and appearance similar to many other foods. For example, soybeans are the primary ingredient in many dairy product substitutes (e.g., soymilk, margarine, soy ice cream, soy yogurt, soy cheese, and soy cream cheese) and meat substitutes (e.g., veggie burgers and tempeh). These substitutes are readily available in most supermarkets. Additionally, soybean cultivar UA54i19GT can be used to produce various types of "fillers" used in meat and poultry products. Food service, retail, and institutional facilities regularly use "extended" products that contain soy fillers.

DEPOSIT INFORMATION

A deposit of the soybean cultivar UA54i19GT disclosed above and recited in the appended claims has been made with the American Type Culture Collection (ATCC), 10801 University Boulevard, Manassas, Va. 20110. The date of deposit was Apr. 1, 2021. The deposit of 2,500 seeds was taken from the same deposit maintained by the Arkansas Agricultural Experiment Station (1371 W. Altheimer Drive, Fayetteville, Ark. 72704) since prior to the filing date of this application. All restrictions will be irrevocably removed upon granting of a patent, and the deposit is intended to meet all of the requirements of 37 C.F.R. §§ 1.801-1.809. The ATCC Accession Number is PTA-127018. The deposit will be maintained in the depository for a period of thirty years, or five years after the last request, or for the enforceable life of the patent, whichever is longer, and will be replaced as necessary during that period.

What is claimed is:

1. A soybean seed of the cultivar 'UA54i19GT,' a representative sample of seed of said cultivar having been deposited under ATCC Accession No. PTA-127018.

2. A soybean plant, or a part thereof, produced by growing the seed of claim 1.

3. A method for producing soybean plants, said method comprising planting a plurality of soybean seeds as recited in claim 1 under conditions favorable for the growth of soybean plants.

4. The method of claim 3, further comprising the step of producing soybean seed from the resulting soybean plants.

5. A soybean seed of the cultivar UA54i19GT produced by the method of claim 4.

6. A tissue culture of regenerable cells or protoplasts produced from the soybean plant of claim 2.

7. A soybean plant regenerated from the tissue culture of claim 6, said soybean plant having the morphological and physiological characteristics of 'UA54i19GT'.

8. A method for producing an $F_1$ hybrid soybean plant, said method comprising crossing a first parent soybean plant with a second parent soybean plant, wherein the first parent soybean plant or the second patent soybean plant is the soybean plant of claim 2.

9. The method of claim 8, further comprising the step of producing soybean seed from the resulting $F_1$ hybrid soybean plant.

10. An $F_1$ hybrid soybean seed produced by the method of claim 9.

11. The method of claim 8, wherein the second parent soybean plant is transgenic.

12. A method comprising transforming the soybean plant of claim 2 or cell thereof with a transgene, wherein the transgene confers at least one trait selected from the group consisting of: herbicide resistance; insect resistance; resistance to bacterial, fungal, or viral disease; modified fatty acid metabolism; modified carbohydrate metabolism; and male sterility.

13. A soybean plant or cell thereof produced by the method of claim 12, wherein the plant or cell comprises the transgene and otherwise comprises all of the morphological and physiological characteristics of a plant or cell of the cultivar UA54i19GT.

14. A method of introducing a desired trait into soybean cultivar 'UA54i19GT,' said method comprising the steps of:
(a) crossing plants as recited in claim 2 with plants of another soybean line expressing the desired trait, to produce progeny plants;
(b) selecting progeny plants that express the desired trait, to produce selected progeny plants;
(c) crossing the selected progeny plants with plants from the 'UA54i19GT parental line to produce new progeny plants;
(d) selecting new progeny plants that express both the desired trait and some or all of the physiological and morphological characteristics of soybean cultivar 'UA54i19GT,' to produce new selected progeny plants; and
(e) repeating steps (c) and (d) three or more times in succession, to produce selected higher generation backcross progeny plants that express both the desired trait and the physiological and morphological characteristics of soybean cultivar 'UA54i19GT,' when grown in the same environmental conditions.

15. The method of claim 14, additionally comprising the step of planting a plurality of soybean seed produced by selecting higher generation backcross progeny plants under conditions favorable for the growth of soybean plants and optionally comprising the step of producing soybean seed from the resulting soybean plants.

16. The soybean seed resulting from the method of claim 15, wherein, if the resulting soybean seed is grown, then the soybean plants grown from the resulting soybean seed express the desired trait and otherwise comprise all of the morphological and physiological characteristics of a plant or cell of the cultivar UA54i19GT.

17. A method of introducing a mutation into the genome of soybean cultivar UA54i19GT, said method comprising applying a mutagen to the plant of claim 2, or a part thereof, wherein said mutagen is selected from the group consisting of ethyl methanesulfonate, gamma-rays, and sodium azide, and wherein the resulting plant comprises a genome mutation.

18. A method of producing a commodity plant product, said method comprising obtaining the plant of claim 1, or a part thereof, and producing said commodity plant product therefrom.

19. The method of claim 18, wherein the commodity plant product is protein concentrate, protein isolate, soybean hulls, meal, flour or oil.

* * * * *